United States Patent
Huck et al.

(10) Patent No.: US 9,980,966 B2
(45) Date of Patent: May 29, 2018

(54) COMBINATIONS OF CANCER THERAPEUTICS

(71) Applicant: Merck Patent GmbH, Darmstadt (DE)

(72) Inventors: Bayard R. Huck, Sudbury, MA (US); Erik Wilker, Lexington, MA (US); Andreas Machl, Cambridge, MA (US); Remigiusz Kaleta, Groton, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days. days.

(21) Appl. No.: 15/128,045

(22) PCT Filed: Mar. 9, 2015

(86) PCT No.: PCT/EP2015/000525
§ 371 (c)(1),
(2) Date: Sep. 21, 2016

(87) PCT Pub. No.: WO2015/149909
PCT Pub. Date: Oct. 8, 2015

(65) Prior Publication Data
US 2017/0100402 A1    Apr. 13, 2017

Related U.S. Application Data

(60) Provisional application No. 61/974,765, filed on Apr. 3, 2014.

(51) Int. Cl.
*A61K 31/517* (2006.01)
*A61K 39/395* (2006.01)
*A61K 39/00* (2006.01)

(52) U.S. Cl.
CPC .......... *A61K 31/517* (2013.01); *A61K 39/395* (2013.01); *A61K 39/39558* (2013.01); *A61K 2039/505* (2013.01); *A61K 2039/545* (2013.01)

(58) Field of Classification Search
CPC ................ A61K 31/517; A61K 39/395; A61K 39/39558
See application file for complete search history.

(56) References Cited

U.S. PATENT DOCUMENTS

2009/0274693 A1    11/2009  Gilmer et al.

FOREIGN PATENT DOCUMENTS

| WO | 2011/144749 A1 | 11/2011 |
| WO | 2012/069146 A1 | 5/2012 |
| WO | 2014/143612 A1 | 9/2014 |

OTHER PUBLICATIONS

Barlund, M. et al., Multiple Genes at 17q23 Undergo Amplification and Overexpression in Breast Cancer, Cancer Res., Oct. 1, 2000, 60:5340-5346.
Berenbaum, M.C., What is synergy? Pharmacol Reviews, 1989, 41:93-141.
Choo A.Y. et al., Rapamycin differentially inhibits S6Ks and 4E-BP1 to mediate cell-type-specific repression of mRNA translation, Proc. Natl Acad Sci U S A, Nov. 11, 2008; 105(45):17414-9.
F. Couch, et al., Localization of PS6K to Chromosomal Region 17q23 and Determination of Its Amplification in Breast Cancer, Cancer Res., 59: 1408-11.
Garcia-Bustos, et al., PIK 1, an essential phosphatidylinositol 4-kinase associated with the yeast nucleus, Embo J., 1994, 13:2352-2361.
C. Garcia-Garcia et al., "Dual mTORC1/2 and HER2 Blockade Results in Antitumor Activity in Preclinical Models of Breast Cancer Resistant to Anti-HER2 Therapy", Clinical Cancer Research, Mar. 8, 2012, vol. 18, No. 9, 2603-2612.
Hanks, S.K., Hunter, T., The eukaryotic protein kinase superfamily: kinase (catalytic) domain structure and classification, FASEB J., 1995, 9:576-596.
Hardie, G. and Hanks, S. (1995) The Protein Kinase Facts Book. I and II, Academic Press, San Diego, CA.
Hiles, et al., Phosphatidylinositol 3-Kinase: Structure and Expression of the 110 kd Catalytic Subunit, Cell, 1992, 70:419-429.
Knighton, et al., Crystal Structure of the Catalytic Subunit of Cyclic Adenosine Monophosphate-Dependent Protein Kinase, Science, 1991, 253:407-414.
Kunz, et al., Target of Rapamycin in Yeast, TOR2, Is an Essential Phosphatidylinositol Kinase Homolog Required for G1 Progression, Cell, 1993, 73:585-596.
Pauwels, B. et al., Comparison of the sulforhodamine b assay and the clonogenic assay for in vitro chemoradiation studies. Cancer chemotherapy and pharmacology, Mar. 2003, 51:221-226.
Tamburini, J. et al., Blood 2008;111:379-82.
Tyle, P. Mammallian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways, Pharmaceutical Research, 1986,3(6):318.
Vichai, V., et al. Sulforhodamine b colorimetric assay for cytotoxicity screening. Nature protocols, Aug. 2006, 1:1112-1116.
A. Vazquez-Martin et al., Low-scale phosphoproteome analyse identify the mTOR effector p70 S6 kinase 1 as a specific biomarker of the dual-HER1/HER2 tyrosine kinase inhibitor lapatinib (Tykerb(R)) in human breast carcinoma pens, Annals of Oncology, Jan. 10, 2008, vol. 19, No. 6, pp. 1097-1109.

*Primary Examiner* — Sahar Javanmard
(74) *Attorney, Agent, or Firm* — Thomas W. Brown; EMD Serono Research and Development Institute

(57) ABSTRACT

The invention relates to combinations of 4-[(S)-2-Azetidin-1-yl-1-(4-chloro-3-trifluoromethyl-phenyl)-ethylamino]-quinazoline-8-carboxylic acid amide and/or its physiologically acceptable salts and solvates, and an inhibitor of Her2, and the use of such combinations for the treatment of cancer.

10 Claims, 2 Drawing Sheets

Evaluation of the effect of combining Compound A with Lapatinib in several cancer cell lines.

Figure 1:
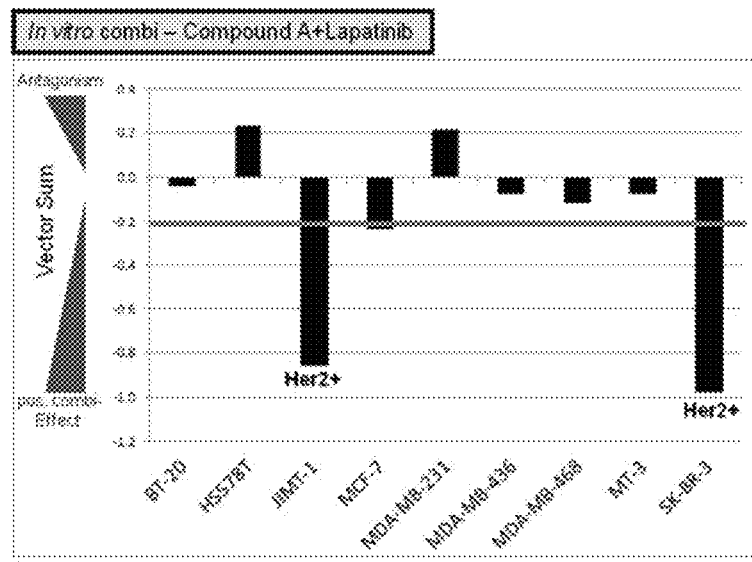

Values for Fig. 1:

| Origin | Cell line | Vector Sum |
|---|---|---|
| breast | BT-20 | -0.0401 |
| breast | HS578T | 0.2342 |
| breast | JIMT-1 | -0.8499 |
| breast | MCF-7 | -0.2349 |
| breast | MDA-MB-231 | 0.2126 |
| breast | MDA-MB-436 | -0.0763 |
| breast | MDA-MB-468 | -0.1157 |
| breast | MT-3 | -0.0745 |
| breast | SK-BR-3 | -0.9705 |

COMBINATIONS OF CANCER THERAPEUTICS

The invention relates to combinations of 4-[(S)-2-Azetidin-1-yl-1-(4-chloro-3-trifluoromethyl-phenyl)-ethylamino]-quinazoline-8-carboxylic acid amide (hereinafter referred to as Compound A) and/or its physiologically acceptable salts and solvates, and inhibitors of the receptor tyrosine-protein kinase erbB-2 also known as HER2 (human epidermal growth factor receptor 2), and the use of such combinations for the treatment of cancer.

BACKGROUND OF THE INVENTION

Compound A, processes for its preparation and its use for the treatment of cancer are disclosed in WO 2012/069146. This compound is a novel selective, highly potent dual inhibitor of p70S6K and Akt, as demonstrated in a variety of cell-based assays.

Compound A was shown to exhibit potent anti-tumor activity against a broad panel of cancer cell lines. Breast cancer cells, glioblastoma cells, endometrial cancer cells and ovarian carcinoma cells are particularly sensitive to Compound A.

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets Akt and PKCζ. Akt directly phosphorylates and inactivates TSC2, thereby activating mTOR. In addition, studies with mutant alleles of p70S6K that are inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indicating that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375). The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/093419, WO 12/013282 and WO 12/069146.

It has been shown that Compound A which does not only inhibit p70S6K but also inhibits kinase Akt (upstream of p70S6K in the PI3K pathway) provides more efficient PI3K pathway shutdown (Choo A Y, Yoon S O, Kim S G, Roux P P, Blenis J. Proc. Natl Acad Sci USA. 2008 Nov. 11; 105(45):17414-9.), and allow for capture of any Akt feedback loop activation (Tamburini et al. Blood 2008; 111:379-82).

The present invention had the objective of finding ways to further advance the pharmaceutical utility for Compound A. In this context, combinations of Compound A with inhibitors of HER2 were studied in vitro and in vivo.

Receptor tyrosine-protein kinase erbB-2 also known as CD340 (cluster of differentiation 340) or proto-oncogene Neu is a protein that in humans is encoded by the ERBB2 gene. The ERBB2 gene is also frequently called HER2 (from human epidermal growth factor receptor.

HER2 is a member of the epidermal growth factor receptor (EGFR/ERBB) family. Amplification or overexpression of this oncogene has been shown to play an important role in the development and progression of certain aggressive types of breast cancer. In recent years the protein has become an important biomarker and target of therapy for approx. 30% of breast cancer patients.

The ErbB family is composed of four plasma membrane-bound receptor tyrosine kinases. All four contain an extracellular ligand binding domain, a transmembrane domain, and an intracellular domain that can interact with a multitude of signaling molecules and exhibit both ligand-dependent and ligand-independent activity. HER2 can heterodimerise with any of the other three receptors and is considered to be the preferred dimerisation partner of the other ErbB receptors. Dimerisation results in the autophosphorylation of tyrosine residues within the cytoplasmic domain of the receptors and initiates a variety of signaling pathways. The other members of the family are Epidermal growth factor receptor, erbB-3 (neuregulin-binding; lacks kinase domain), and erbB-4.

Signaling pathways activated by HER2 include: mitogen-activated protein kinase (MAPK) and phosphoinositide 3-kinase (PI3K/Akt.

In summary, signaling through the ErbB family of receptors promotes cell proliferation and opposes apoptosis, and therefore must be tightly regulated to prevent uncontrolled cell growth from occurring.

Amplification or over-expression of the ERBB2 gene occurs in approximately 15-30% of breast cancers. It is strongly associated with increased disease recurrence and a poor prognosis. Over-expression is also known to occur in ovarian, stomach, and aggressive forms of uterine cancer, such as uterine serous endometrial carcinoma.

Furthermore, diverse structural alterations have been identified that cause ligand-independent firing of this receptor, doing so in the absence of receptor over-expression. HER2 is found in a variety of tumors and some of these tumors carry point mutations in the sequence specifying the transmembrane domain of HER2. Substitution of a valine for a glutamic acid in the transmembrane domain can result in the constitutive dimerization of this protein in the absence of a ligand.

Surprisingly, it has been found by the inventors of the present patent application that Compound A acts in a synergistic way when combined with HER2 inhibitors.

An example of an inhibitor of HER2 is the monoclonal antibody trastuzumab (marketed as Herceptin). Trastuzumab is a highly purified recombinant DNA-derived humanized monoclonal IgGI kappa antibody that binds with high affinity and specificity to the extracellular domain of the HER2 receptor. It has been approved for the treatment of cancers where HER2 is over-expressed.

An example of a small molecule inhibitor of HER2 is lapatinib (marketed as Tyverb).

FIGURES

FIG. 1: Evaluation of the effect of combining Compound A with Lapatinib in several cancer cell lines.

Figure 2:
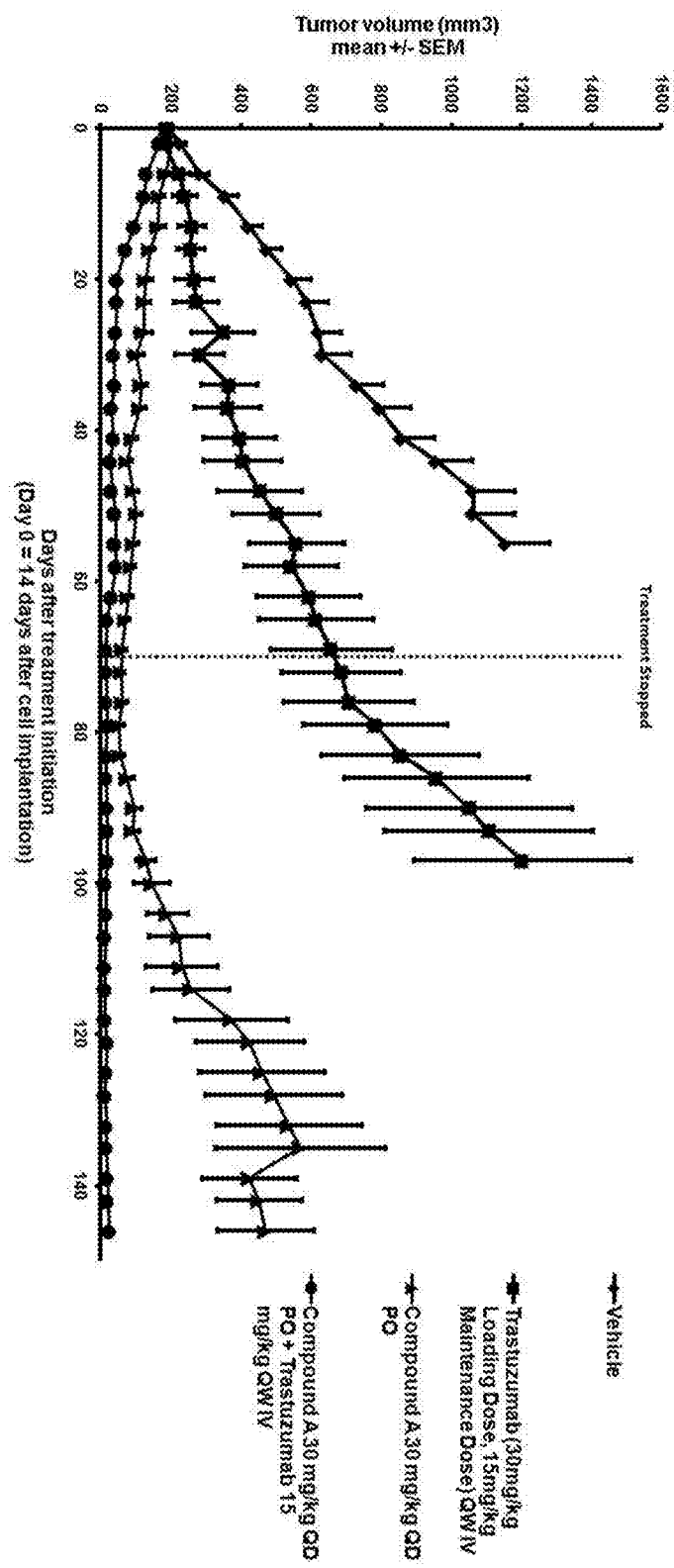

FIG. 2: Evaluation of the effect of combining Compound A with Trastuzumab in a patient derived xenograft model of breast cancer

DETAILED DESCRIPTION OF THE INVENTION

The present invention relates to a method for prophylaxis and/or treatment of cancers where HER2 is over-expressed (Her2+ cancers), comprising administering to a subject Compound A and/or its physiologically acceptable salts and solvates, and one or more inhibitors of Her2.

Compound A and/or its physiologically acceptable salts and solvates, and the Her2 inhibitor can be administered simultaneously or sequentially. When administered simultaneously, Compound A and/or its physiologically acceptable salts and solvates, and the Her2 inhibitor may be administered as a compound mixture in one pharmaceutical composition or as separate pharmaceutical compositions.

In a preferred embodiment, the method according to the invention comprises the use of Compound A and/or its physiologically acceptable salts and solvates, and one Her2 inhibitor which are administered sequentially. In a further preferred embodiment, the Her2 inhibitor is administered first.

The present invention relates in particular to a method for prophylaxis and/or treatment of tumors selected from the group consisting of HER2+ breast cancer, gastric or gastroesophageal junction adenocarcinoma. However, the treatment method also relates to other HER2+ tumor types that present response on trastuzumab such as bladder cancer, lung cancer, ovarian cancer, endometrial cancer, esophageal cancer, salivary gland cancer etc., or other tumors that respond to treatment with trastuzumab based on their molecular profile.

In a preferred embodiment the methods according to the present invention relate to the treatment of cancer and, in particular, to the tumors described hereinabove and below.

Moreover, the present invention relates to a pharmaceutical composition, comprising a compound mixture of the active pharmaceutical ingredients (API's) Compound A, and physiologically acceptable salts and solvates thereof, and one Her2 inhibitor. If the Her2 inhibitor is a small chemical molecule, such as lapatinib (as opposed to a biological molecule, such as an antibody, antibody fragment or antibody conjugate), the compound mixture in the pharmaceutical composition may also comprise physiologically acceptable salts and solvates of this small molecule Her2 inhibitor.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates, benzoates or p-toluenesulfonates.

Solvates of Compound A and small molecule Her2 inhibitors are taken to mean adductions of inert solvent molecules onto Compound A which form owing to their mutual attractive force. Solvate are, for example, hydrates, such as monohydrates or dihydrates, or alcoholates, i.e. addition compounds with alcohols, such as, for example, with methanol or ethanol.

A preferred salt form of Compound A its free base. Also preferred are its hydrochloride, dihydrochloride, mesylate, succinate or malonate salts.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or prevention of side effects or also reduction in the progress of a disease, condition or disorder. The term "therapeutically effective amount" also encompasses the amounts which are effective for increasing normal physiological function.

The pharmaceutical composition according to the invention comprise mixtures of two API's, for example in the ratio 1:1, 1:2, 1:3, 1:4, 1:5, 1:10, 1:100 or 1:1000.

The pharmaceutical composition furthermore comprises at least one solid, liquid and/or semi-liquid excipient or adjuvant. Therefore, the invention also relates to a pharmaceutical composition comprising the said API mixture according to the invention and the said excipients and/or adjuvants.

Furthermore, the present invention relates to the use of the said pharmaceutical composition for the preparation of a medicament for the treatment of cancer.

The invention also relates to a set (kit) consisting of separate packs of
(a) a pharmaceutical composition comprising an effective amount of Compound A,
(b) a pharmaceutical composition comprising an effective amount of a Her2 inhibitor and, optionally,
(c) a pharmaceutical composition comprising an effective amount of a third cancer therapeutic.

The set comprises suitable containers, such as boxes, individual bottles, bags or ampoules. The set may, for example, comprise separate ampoules, each containing a pharmaceutical composition comprising an effective amount of Compound A and/or pharmaceutically usable salts thereof, a pharmaceutical composition comprising an effective amount of the Her2 inhibitor and/or pharmaceutically usable salts thereof and, optionally, a pharmaceutical composition comprising an effective amount of another cancer therapeutic in dissolved or lyophilised form.

Cancer therapeutics that can be combined with Compound A and the Her2 inhibitor, according to the invention, may include one or more, but preferably one, of the following agents:

Alkylating agents, such as altretamine, bendamustine, busulfan, carmustine, chlorambucil, chlormethine, cyclophosphamide, dacarbazine, ifosfamide, improsulfan tosilate, lomustine, melphalan, mitobronitol, mitolactol, nimustine, ranimustine, temozolomide, thiotepa, treosulfan, mechloretamine, carboquone, apaziquone, fotemustine, glufosfamide, palifosfamide, pipobroman, trofosfamide, uramustine;

Platinum Compounds, such as carboplatin, cisplatin, eptaplatin, miriplatine hydrate, oxaliplatin, lobaplatin, nedaplatin, picoplatin, satraplatin;

DNA altering agents, such as amrubicin, bisantrene, decitabine, mitoxantrone, procarbazine, trabectedin, clofarabine, amsacrin, brostallicin, pixantrone, laromustine;

Topoisomerase inhibitors, such as etoposide, irinotecan, razoxane, sobuzoxane, teniposide, topotecan, amonafide, belotecan, elliptinium acetate, voreloxin;

Microtubule modifiers, such as cabazitaxel, docetaxel, eribulin, ixabepilone, paclitaxel, vinblastine, vincristine, vinorelbine, vindesine, vinflunine, fosbretabulin, tesetaxel;

Antimetabolites, such as asparaginase, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur, doxifluridine, elacytarabine, raltitrexed, sapacitabine, tegafur, trimetrexate;

Anticancer antibiotics, such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin, aclarubicin, peplomycin, pirarubicin;

Hormones/Antagonists, such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol, acolbifene, danazol, deslorelin, epitiostanol, orteronel, enzalutamide;

Aromatase inhibitors, such as aminoglutethimide, anastrozole, exemestane, fadrozole, letrozole, testolactone, formestane;

Small molecule kinase inhibitors, such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib, afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib, cabozantinib S-malate, carfilzomib, ibrutinib, icotinib;

Photosensitizers. such as methoxsalen, porfimer sodium, talaporfin, temoporfin;

Antibodies, such as alemtuzumab, besilesomab, brentuximab vedotin, cetuximab, denosumab, ipilimumab, ofatumumab, panitumumab, rituximab, tositumomab, trastuzumab, bevacizumab, catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab, onartuzumab, pertuzumab, racotumomab, tabalumab;

Cytokines, such as aldesleukin, interferon alfa, interferon alfa2a, interferon alfa2b, tasonermin, teceleukin, oprelvekin;

Drug conjugates, such as denileukin diftitox, ibritumomab tiuxetan, iobenguane 1123, prednimustine, trastuzumab emtansine, estramustine, gemtuzumab ozogamicin, aflibercept, cintredekin besudotox, edotreotide, inotuzumab ozogamicin, naptumomab estafenatox, oportuzumab monatox, technetium (99mTc) arcitumomab, vintafolide;

Vaccines, such as sipuleucel, vitespen, emepepimut-S, oncoVAX, rindopepimut, troVax, stimuvax;

Miscellaneous agents, such as alitretinoin, bexarotene, bortezomib, everolimus, ibandronic acid, imiquimod, lenalidomide, lentinan, metirosine, mifamurtide, pamidronic acid, pegaspargase, pentostatin, sipuleucel, sizofiran, tamibarotene, temsirolimus, thalidomide, tretinoin, vismodegib, zoledronic acid, thalidomide, vorinostat, celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine, picibanil, reolysin, retaspimycin hydrochloride, trebananib, virulizin.

Particularly preferred combination partners of Compound A and the Her2 inhibitor are Her3 inhibitors, such as MM-121 (a fully humanized anti-Her3 antibody that specifically blocks the binding of HRG1—(a neuregulin-1 type I polypeptide) to Her3, MM-111 (a bispecific antibody, binding to two different target proteins, ErbB2 and ErbB3), or U3-1287 (AMG888, the first fully humanized Her3 monoclonal antibody), or Her3 nanobodies as described in WO 2011/144749.

The compounds and compound mixtures according to the invention can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such medicaments can be prepared using all processes known in the pharmaceutical art by, for example, combining the active ingredient with the excipient(s) or adjuvant(s).

Compounds and compound mixtures adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the compound or compound mixtures can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the compound or compound mixtures after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds and compound mixtures according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compounds and compound mixtures in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil, or natural sweeteners or saccharin or other artificial sweeteners, and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds and compound mixtures according to the invention and salts and solvates thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds and compound mixtures according to the invention can also be delivered using monoclonal antibodies as individual carriers to which the compound molecules are coupled. The compounds and compound mixtures can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Compounds and compound mixtures adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6):318, 1986.

Compounds and compound mixtures adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the compounds or compound mixtures can be employed either with a paraffinic or a water-miscible cream base. Alternatively, the compounds or compound mixtures can be formulated to give a cream with an oil-in-water cream base or a water-in-oil base.

Compounds and compound mixtures adapted for topical application to the eye include eye drops, in which the active ingredient is dissolved or suspended in a suitable carrier, in particular an aqueous solvent.

Compounds and compound mixtures adapted for topical application in the mouth encompass lozenges, pastilles and mouthwashes.

Compounds and compound mixtures adapted for rectal administration can be administered in the form of suppositories or enemas.

Compounds and compound mixtures adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Compounds and compound mixtures adapted for administration by inhalation encompass finely particulate dusts or mists, which can be generated by various types of pressurised dispensers with aerosols, nebulisers or insufflators.

Compounds and compound mixtures adapted for vaginal administration can be administered as pessaries, tampons, creams, gels, pastes, foams or spray formulations.

Compounds and compound mixtures adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the medicaments according to the invention may also comprise other agents usual in the art with respect to the particular type of pharmaceutical formulation; thus, for example, compounds or compound mixtures which are suitable for oral administration may comprise flavours.

A therapeutically effective amount of a compound or compound mixture of the present invention depends on a number of factors, including, for example, the age and weight of the recipient, the precise condition that requires treatment, and its severity, the nature of the formulation and the method of administration, and is ultimately determined by the treating doctor or vet. However, an effective amount of an API for the treatment of the diseases according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as a fraction of the effective amount of the compounds and compound mixtures according to the invention per se.

The pharmaceutical preparations according to the invention can be employed as medicaments in human and veterinary medicine. Suitable excipients are organic or inorganic substances which are suitable for enteral (for example oral), parenteral or topical administration and do not react with the novel compounds, for example water, vegetable oils, benzyl alcohols, polyethylene glycols, gelatine, carbohydrates, such as lactose or starch, magnesium stearate, talc or Vaseline. Suitable for enteral administration are, in particular, tablets, coated tablets, capsules, syrups, juices, drops or suppositories, suitable for parenteral administration are solutions, preferably oil-based or aqueous solutions, furthermore suspensions, emulsions or implants, and suitable for topical application are ointments, creams or powders. The compounds and compound mixtures may also be lyophilised and the resultant lyophilisates used, for example, for the preparation of injection preparations.

The preparations indicated may be sterilised and/or comprise adjuvants, such as lubricants, preservatives, stabilisers and/or wetting agents, emulsifiers, salts for modifying the osmotic pressure, buffer substances, dyes, flavours and/or aroma substances. They can, if desired, also comprise one or more further active ingredients, for example one or more vitamins.

EXAMPLES

The examples below relate to pharmaceutical preparations:

Example A1: Injection Vials

A solution of 100 g of a compound or a compound mixture according to the invention and 5 g of disodium hydrogenphosphate in 3 l of bidistilled water is adjusted to pH 6.5 using 2N hydrochloric acid, sterile filtered, transferred into injection vials, lyophilised and sealed under sterile conditions. Each injection vial contains 5 mg of active ingredients.

Example A2: Suppositories 20 g of a compound or a compound mixture according to the invention is melted with 100 g of soya lecithin and 1400 g of cocoa butter, poured into moulds and allowed to cool. Each suppository contains 20 mg of active ingredients.

Example A3: Solution

A solution is prepared from 1 g of a compound or a compound mixture according to the invention, 9.38 g of $NaH_2PO_4 \times 2H_2O$, 28.48 g of $NaH_2PO_4 \times 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example A4: Ointment 500 mg of a compound or a compound mixture according to the invention are mixed with 99.5 g of Vaseline under aseptic conditions.

Example A5: Tablets 1 kg of a compound or a compound mixture according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredients.

Example A6: Coated Tablets

Tablets are pressed analogously to Example E and subsequently coated in a conventional manner with a coating of sucrose, potato starch, talc, tragacanth and dye.

Example A7: Capsules 2 kg of a compound or a compound mixture according to the invention are introduced into hard gelatine capsules in a conventional manner in such a way that each capsule contains 20 mg of the active ingredients.

Example A8: Ampoules

A solution of 1 kg of a compound or a compound mixture according to the invention in 60 l of bidistilled water is transferred into ampoules, lyophilised under aseptic conditions and sealed under sterile conditions. Each ampoule contains 10 mg of active ingredients.

The following examples relate to combination studies using Compound A and Her2 inhibitors.

Example B1: Combination of Compound A and Lapatinib in Nine Human Breast Cancer Cell Lines Experimental Procedure for Cell Culture and Growth Inhibition Assay:

The cell lines were grown in the media recommended by the suppliers in the presence of 100 U/ml penicillinG and 100 µg/ml streptomycin supplied with 10% FCS (PAN, Germany).

Cell growth and treatment were performed in 96-well microtitre plates. Cells harvested from exponential phase cultures by trypsinization were plated in 190 µl of media at optimal seeding densities. The optimal seeding densities for each cell line were determined to ensure exponential growth for the duration of the experiment. All cells growing without anticancer agents were sub-confluent by the end of the treatment as determined by visual inspection. Compound dilutions in DMSO were performed in 96-well rigid PCR plates. Compounds were then diluted 1:50 in RPMI medium. 190 µl of cells, after a 24-hour pre-growth period, were treated by mixing with 10 µl of the compound-containing media (resulting in a final DMSO concentration of 0.1%). The cells were allowed to grow at 37° C. for 72 hours. In addition, all experiments contained a few plates with cells that were processed for measurement immediately after the 24 hours recovery period. These plates contained information about the cell number that existed before treatment, at time zero, and served to calculate the cytotoxicity and/or growth inhibitory effects. After treatment, cells were precipitated by addition of 10% TCA. Prior to fixation, the media was aspirated as described [Pauwels et al., 2003]. After an hour of incubation at 4° C. the plates were washed two times with 400 µl of deionized water. Cells were then stained with 100 µl of a 0.08% wt/v SRB. The plates were allowed to sit for at least 30 min and washed six times with 1% acetic acid to remove unbound stain [Vichai and Kirtikara, 2006]. The plates were left to dry at room temperature and bound SRB was solubilized with 100 µl of 10 mM Tris base. Measurement of optical density was performed at 560 nm on a Victor 2 plate reader (Perkin Elmer, Germany).

Experimental Design:

Prior to in vitro combination studies, the activity of individual agents was investigated using a panel of 80 cell lines. This concentration range provided guidance for selecting the concentration range for specific cell lines. The combination was tested by combining a matrix of Lapatinib in the concentrations and Compound A in the concentrations in a 96 well plate. The agents were added simultaneously to the cells.

The concentrations of the compounds used are listed in the table below:

| Concentrations of compounds in Mol [M] | |
| --- | --- |
| Lapatinib | Compound A |
| 0.00E+00 | 0.000E+00 |
| 2.50E−07 | 1.000E−07 |
| 5.00E−07 | 2.000E−07 |
| 1.00E−06 | 4.000E−07 |
| 2.00E−06 | 8.000E−07 |
| 4.00E−06 | 1.600E−06 |
| 8.00E−06 | 3.200E−06 |

Pairwise combination of Compound A with Lapatinib were tested in all cell lines using a 6×6 matrix. The screening was designed to determine potential synergistic combinations. All and/or part of the 6×6 matrix were used to design the study.

The methods to calculate synergy can be found in [Berenbaum, 1989]. The following parameters were calculated $$\delta_i = Measuredvalue_i - Theoretical\ value_i$$

where i=[1 . . . n] is one of the values of the matrix used and Theoretical value i calculated as described for the Bliss Independence method [Berenbaum, 1989].

Vector sum was determined as $$Vector\ sum = \sum_{i=1}^{n} Sign(Effect_i)Effect_i^2$$

in this term the VectorSum rather represents scalar $$Vector\ sum\ average = \frac{1}{n}\sum_{i=1}^{n} Effect_i = Mean(Effect_i)$$

The average values below −0.5 indicate a strong synergy effect: (−0.5, −0.02]—synergy effect, (−0.02, 0.02)—zero effect (additivism), (0.02, 0.5)—potential antagonism, and above 0.5—strong antagonism.

Literature
M. C. Berenbaum. What is synergy? Pharmacol Reviews, 41:93-141, 1989.
Bea Pauwels, Annelies E. C. Korst, Christel M. J. de Pooter, Greet G. O. Pattyn, Hilde A. J. Lambrechts, Marc F. D. Baay, Filip Lardon, and Jan B. Vermorken. Comparison of the sulforhodamine b assay and the clonogenic assay for in vitro chemoradiation studies. Cancer chemotherapy and pharmacology, 51:221-226, March 2003.
Vanicha Vichai and Kanyawim Kirtikara. Sulforhodamine b colorimetric assay for cytotoxicity screening. Nature protocols, 1:1112-1116, August 2006.

Example B2: Combination of Compound A and Trastuzumab in a Patient Derived Xenograft Model of Breast Cancer Female nude (Harlan; nu/nu) between 5-7 weeks were implanted subcutaneously with tumor fragments from the Her2+ patient-derived breast model "CTG-0033" (passage 3, i.e. the model has been serially passaged/grown from the original host 3 times) harvested from host animals. When host tumors reached 1-1.5 cm$^3$, tumors were harvested for re-implantation into animals to be used for the efficacy study. When the CTG-0033 (passage 4) tumors reached approximately 190 mm$^3$; animals were randomized by tumor volume into treatment or control groups (n=10) and dosing was initiated on Day 0. Treatments were Vehicle (Saline), Compound A 30 mg/kg QD (daily) PO (per oral), Herceptin (30 mg/kg loading dose and 15 mg/kg maintenance dose) QW (per week) IV (intravenous), and Compound A 30 mg/kg QD PO in combination with Herceptin 15 mg/kg QW IV. Tumor volumes were recorded twice per week. Vehicle treatment group was terminated at Day 55 due to large tumors. The other treatments were stopped at Day 75 and tumors were allowed to grow back for over 2 months with mice receiving no treatment. Two animals died in this study. One animal in the Compound A group died at day 9 due to a suspected gavage error and the other in the Compound A+Herceptin group due to human error.

Treatment with Compound A 30 mg/kg (monotherapy group) resulted in 50 percent tumor regression while treatment with Compound A+Herceptin resulted in 78% regression at Day 55. Treatment with Herceptin resulted in a % T/C of 37 at Day 55. Treatment with Compound A+Herceptin significantly inhibited tumor growth as compared to the single agents Herceptin and Compound A (P<0.05; 2 Way RM-ANOVA Bonferonni Post Hoc Test) at Day 55). While the Vehicle group was stopped, animals continued to receive Compound A, Herceptin, or Compound A+Herceptin until Day 75 and tumors were allowed to grow back. At Day 76, treatment with Compound A resulted in −66% regression while the combination group had completely regressed (tumor volumes less than 40 mm3). After 71 days of regrowth period after the cessation of treatment, 6 of the Compound A treated tumors grew back while none of the combination treatment tumors grew back. This difference in the grow-back of the tumors treated with Compound A compared to Compound A and Herceptin was statistically significant (log rank sum test p<0.05). All of the animals in the combination group were considered cured as tumors did not grow back.

The invention claimed is:

1. A method for the prophylaxis or treatment of cancer comprising administering to a subject 4-[(S)-2-Azetidin-1-yl-1-(4-chloro-3-trifluoromethyl-phenyl)-ethylamino]-quinazoline-8-carboxylic acid amide, or physiologically acceptable salts thereof, and a Her2 inhibitor, or physiologically acceptable salts thereof, wherein the cancer is selected from the group consisting of breast, gastric, and uterine.

2. The method according to claim 1 wherein in the cancer is human breast cancer.

3. The method according to claim 1, wherein 4-[(S)-2-Azetidin-1-yl-1-(4-chloro-3-trifluoromethyl-phenyl)-ethyl-amino]-quinazoline-8-carboxylic acid amide and the Her2 inhibitor are administered simultaneously.

4. The method according to claim 1, wherein 4-[(S)-2-Azetidin-1-yl-1-(4-chloro-3-trifluoromethyl-phenyl)-ethyl-amino]-quinazoline-8-carboxylic acid amide and the Her2 inhibitor are administered sequentially.

5. The method according to claim 4, wherein the Her2 inhibitor is administered first.

6. The method according to claim 2, wherein 4-[(S)-2-Azetidin-1-yl-1-(4-chloro-3-trifluoromethyl-phenyl)-ethyl-amino]-quinazoline-8-carboxylic acid amide and the Her2 inhibitor are administered simultaneously.

7. The method according to claim 2, wherein 4-[(S)-2-Azetidin-1-yl-1-(4-chloro-3-trifluoromethyl-phenyl)-ethyl-amino]-quinazoline-8-carboxylic acid amide and the Her2 inhibitor are administered sequentially.

8. The method according to claim 7, wherein the Her2 inhibitor is administered first.

9. The method of any one of claim 1-5 or 6-8, wherein the Her2 inhibitor is trastuzumab.

10. The method of any one of claim 1-5 or 6-8, wherein the Her2 inhibitor is lapatinib.

\* \* \* \* \*